United States Patent [19]

Moskal

[11] Patent Number: 5,615,953
[45] Date of Patent: Apr. 1, 1997

[54] BOILER BANK SURFACE TEMPERATURE PROFILER

[75] Inventor: Thomas E. Moskal, Pickerington, Ohio

[73] Assignee: The Babcock & Wilcox Company, New Orleans, La.

[21] Appl. No.: 279,736

[22] Filed: Jul. 25, 1994

[51] Int. Cl.$^6$ .......................... G01N 25/00; G01K 1/14; G01K 13/00

[52] U.S. Cl. .............. 374/7; 374/124; 374/131; 374/141; 134/57 R; 134/167 C

[58] Field of Search ............... 374/5, 6, 7, 124, 374/131, 166, 45, 141; 134/57 R, 167 C, 168 C

[56] References Cited

U.S. PATENT DOCUMENTS

| | | | |
|---|---|---|---|
| 3,511,091 | 5/1970 | Thome | 374/147 |
| 3,544,710 | 12/1970 | Poos | 178/6 |
| 4,098,122 | 7/1978 | Landman et al. | |
| 4,176,554 | 12/1979 | Kazmierowicz | |
| 4,412,090 | 10/1983 | Kawate et al. | 136/230 |
| 4,666,245 | 5/1987 | Pointer | 374/131 |
| 4,854,724 | 8/1989 | Adams et al. | 374/124 |
| 4,872,762 | 10/1989 | Koshihara et al. | 374/124 |
| 5,094,695 | 3/1992 | Bailey et al. | 134/18 |
| 5,096,502 | 3/1992 | Carter et al. | 134/18 |
| 5,110,365 | 5/1992 | Carter | 134/18 |
| 5,156,461 | 10/1992 | Moslehi et al. | 374/124 |
| 5,219,226 | 6/1993 | James | 374/124 |
| 5,248,198 | 9/1993 | Droege | 374/7 |

FOREIGN PATENT DOCUMENTS 0081469  7/1981  Japan ..................... 374/131

OTHER PUBLICATIONS

Promotional Brochure, EXERGEN Corp, "Infrared Thermocouples–Temperature Without Touching", admitted prior art (no date).
Promotional Brochure, Williamson Corp., "Noncontact Temperature Measurement Systems" admitted prior art (no date).

Primary Examiner—Diego F. F. Gutierrez
Attorney, Agent, or Firm—Robert P. Bennett, Jr.; Robert J. Edwards

[57] ABSTRACT

A system for determining the cleanliness of a boiler having a plurality of tube banks by obtaining a temperature profile of the boiler heat transfer surfaces includes extending an extension arm, such as a soot blower lance, near the tube banks of the boiler. A separate temperature reading is taken at intervals along the length of the extension arm by utilizing either a plurality of infrared non-contact temperature sensors or a plurality of optical fibers. Each separate temperature reading enables a temperature profile to be determined along the length of the extension arm which, in turn, allows deposit accumulation on the tube banks to be determined.

7 Claims, 9 Drawing Sheets

BOILER BANK SURFACE TEMPERATURE PROFILER

BACKGROUND OF THE INVENTION

1. Field of the Invention

The present invention relates, in general, to measuring temperature profiles and, in particular, to a new and useful system and method for measuring the temperature profile along an extension arm located near a bank of boiler tubes in order to determine the amount of build-up and deposits on the tubes.

2. Description of the Related Art

In the power plant field, several systems and methods have been used in order to determine temperature profiles for the internals of boilers and gas furnaces.

U.S. Pat. No. 4,098,122 discloses a gas temperature probe for use in a blast furnace comprising two tubes which are connected to each other at one end within the walls of the blast furnace. Each tube supports a plurality of thermocouples which extend from the tube in a spaced relationship along the length of the tube. The thermocouples are connected to a recording apparatus which records the temperature profile sensed by the thermocouples.

U.S. Pat. No. 4,176,554 discloses a method and apparatus for obtaining a temperature profile of a kiln. The apparatus comprises a temperature probe having a plurality or array of spaced thermocouples thereon. The probe is inserted into the kiln and the thermocouples are operatively connected to a CRT which displays the temperature profile of the kiln on a continuous basis.

U.S. Pat. No. 5,219,226 discloses an imaging and temperature monitoring system which comprises a sensor which is located in a temperature environment. The sensor has a video imager which produces a video image of the environment. A pyrometer is also included in the sensor which is operatively connected to a computer controller which allows the pyrometer to directly collect temperature information from various regions of the environment.

U.S. Pat. No. 3,544,710 discloses a method of controlling the operation of a shaft furnace comprising a television camera which is sensitive to infrared radiation. The television camera is operatively connected to a computer which measures and displays the temperature profile provided by the camera.

Presently, there is no known system or method for determining the amount of deposits on a bank of boiler tubes. The method comprises utilizing a temperature profile taken from an extension arm probe placed near the bank of tubes.

SUMMARY OF THE INVENTION

The present invention is a system and method for obtaining a temperature profile for a bank of boiler tubes in order to determine the amount of build-up on the tubes. The system and method comprises utilizing an extension arm probe which is extendable into the boiler near the bank of tubes. The extension arm probe may be a lance of a soot blower, an extension arm of an internal camera viewing system, or an extension arm which would appear similar to a soot blower, however, the extension arm would have no other purpose than to probe the boiler tube bank at a particular location and to obtain the temperature profile at that location. Such an extension arm probe may be referred to hereinafter as a "dedicated probe".

The extension arm probe includes a plurality of temperature reading means spaced along the length of the extension arm for taking a separate temperature reading at each location along the length of the extension arm. Temperature readings are taken by utilizing a plurality of infrared non-contact temperature sensors which are spaced along the length of the extension arm and which are sensitive to infrared radiation. The infrared non-contact temperature sensors can also be positioned at an incline along the length of the extension arm for obtaining a different sensing angle. An infrared monitor senses the infrared radiation signal received from each infrared non-contact temperature sensor. A computer is operatively connected to the monitor.

Another embodiment of the temperature reading means includes a plurality of optical fibers which are embedded into the outer surface of the extension arm probe along a plurality of locations. The optical fibers receive infrared light and transmit the light to infrared non-contact temperature sensors located outside of the extension arm probe, and therefore outside of the harsh environment of the boiler flue gas. An infrared monitor is operatively connected to each infrared non-contact temperature sensor for monitoring the infrared radiation signal received from each infrared non-contact temperature sensor. A computer is operatively connected to the monitor for determining temperature profile.

The amount of build-up or deposits on the tubes of the tube banks can be determined by the computer by utilizing the separate temperature readings sensed by the monitor and by inputting the temperature of the water or steam within the tubes. For instance, an average deposit surface temperature is determined together with an estimate of the tube wall temperature beneath any deposits or build-up and an estimated thermal conductivity of the deposits which is used to infer the thickness of the deposits or build-up.

One embodiment of the extension arm probe includes a lance of a soot blower system which is retractably movable within the soot blower system. The lance includes means for removing the deposits from the tube banks. The deposits or soot can be easily removed through the use of air, cleaning liquid, water or steam.

A second embodiment of the extension arm probe is an extension arm for an internal viewing camera in which the camera is mounted within the extension arm for viewing the internals of the boiler.

A third embodiment of the extension arm probe is an extension arm which would appear similar to a soot blower; however, the extension arm probe would have no other purpose than to probe the boiler tube bank at a particular location and to obtain the temperature profile at that location. For all three embodiments, the temperature reading means, i.e. the optical fibers or infrared non-contact temperature sensors, are spaced along the length of the lance, camera extension arm, or dedicated probe, respectively.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
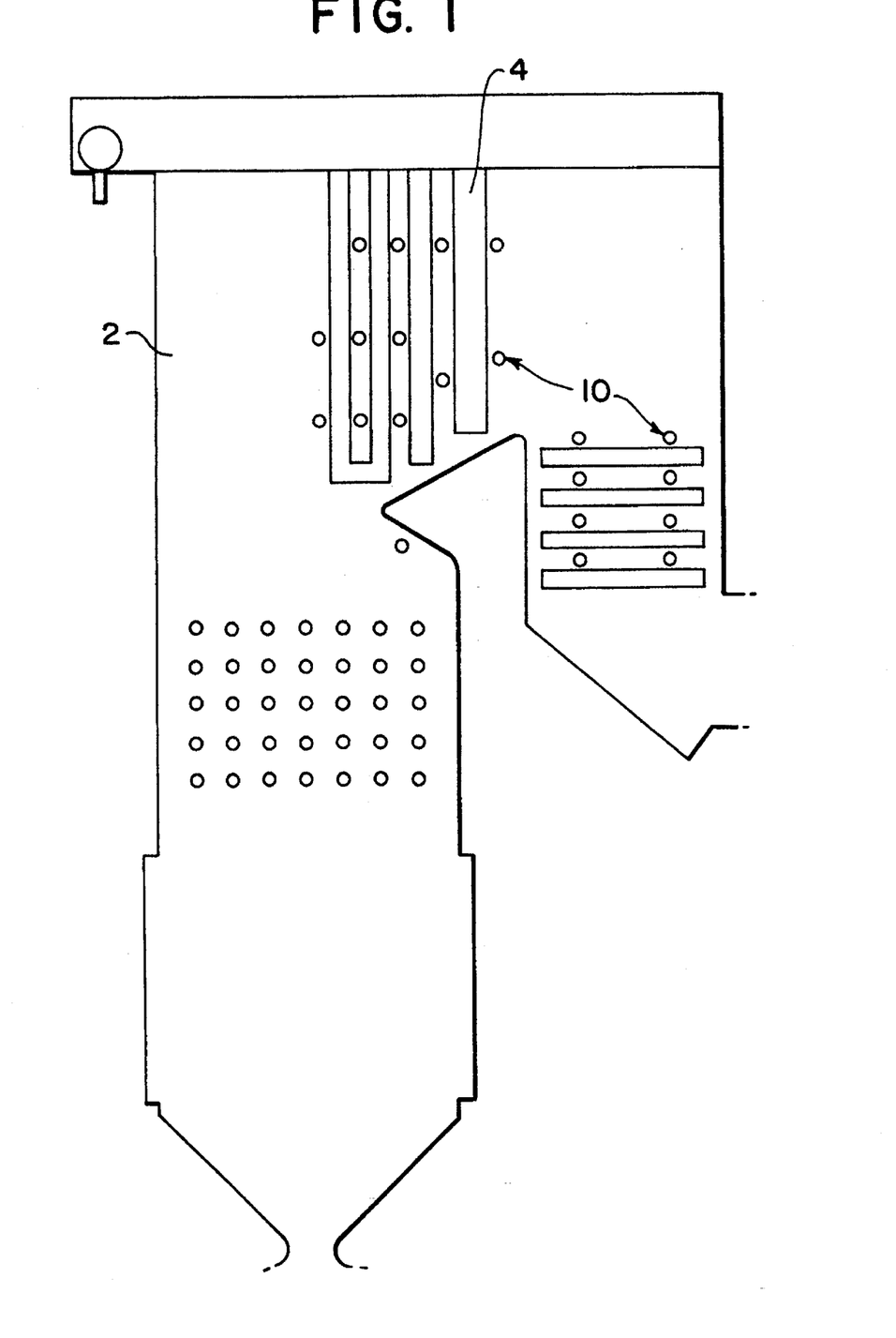
FIG. 1 is a schematic view illustrating a boiler utilizing the present invention.
Figure 3:
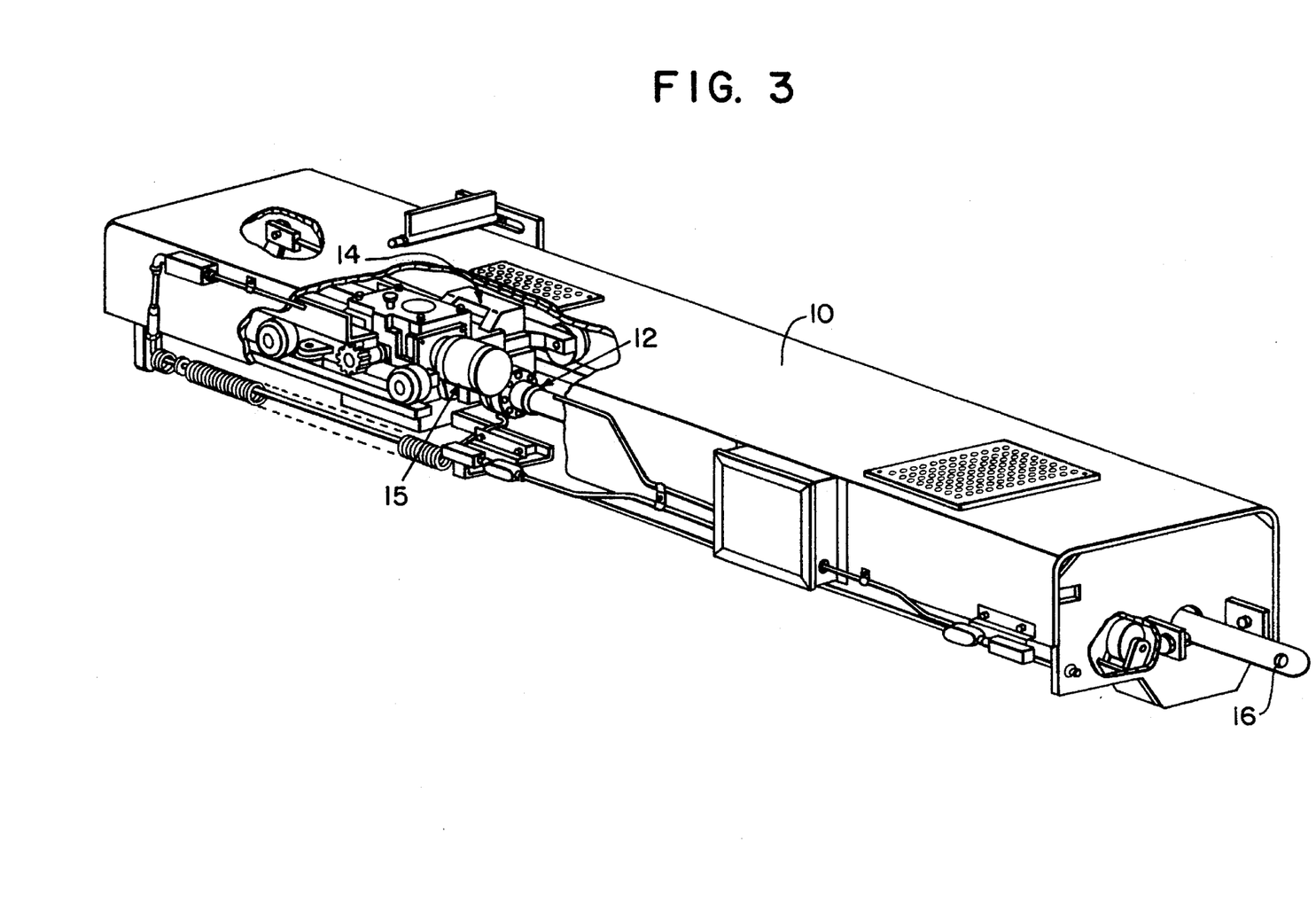
FIG. 3 is a perspective view illustrating a soot blower system.

The present invention is a system and method used in conjunction with a boiler 2 in order to determine the temperature profile of tube banks 4 used in the boiler 2 as shown in FIG. 1. The present invention provides for the portable measurement of the temperature profile of the tube banks 4 in order to determine an immediate on-line assessment of the cleaning effectiveness of deposit or build-up removal equipment such as a soot blower system 10 as illustrated in FIG. 3.

Figure 2:
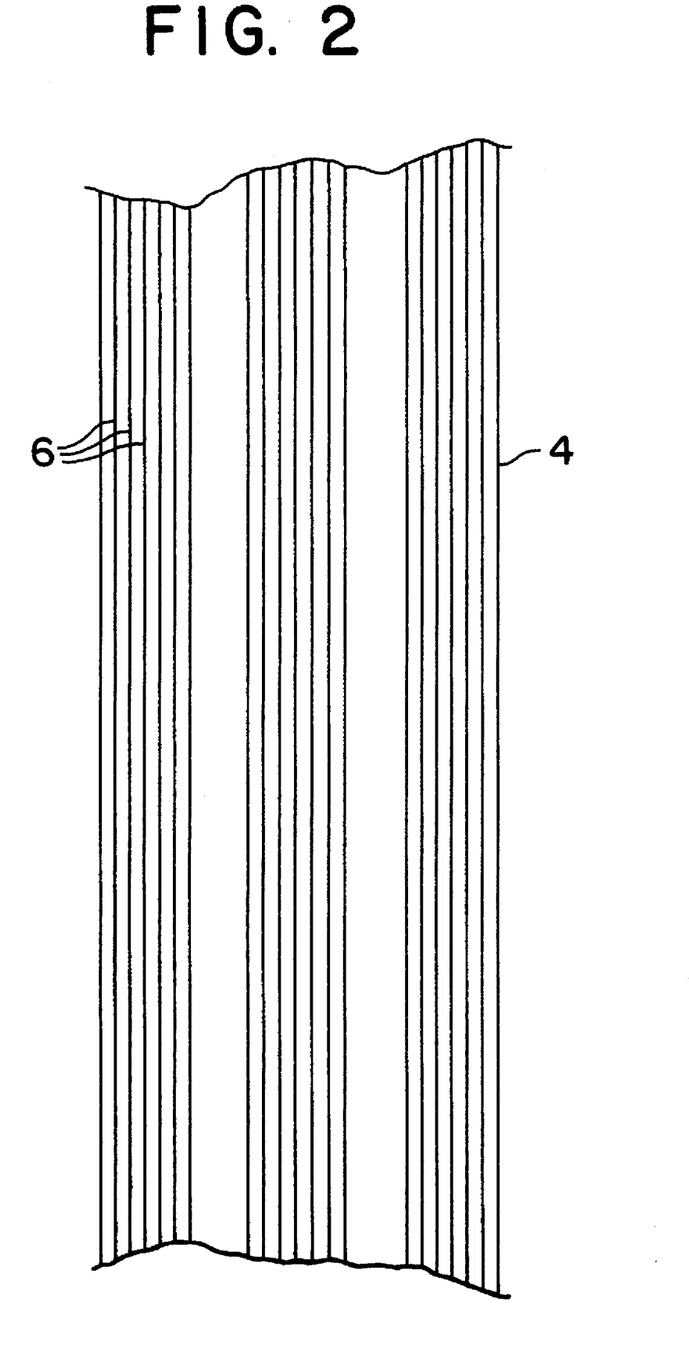
FIG. 2 is a schematic view illustrating a plurality of tube banks for the boiler of FIG. 1.

The present invention eliminates the need to utilize high cost and time-consuming methods such as installing permanent heat flux sensors or steam side thermocouples for the tubes 6 of the tube banks 4 (FIG. 2). FIG. 3 shows the soot blower system 10 comprising a lance 12 mounted to carriage 14 for retractably moving the lance 12 from the system casing 10 by motor 15 in order to locate the lance 12 near each tube bank 4 (FIG. 1) in order to clean deposits and build-up from the tube banks 4 by spraying steam, cleaning liquid, water or air through nozzle 16 of the lance 12.

In order to make an accurate determination of the temperature profile of each tube bank 4, the lance 12 includes a plurality of optical fibers 24, 26 and 28 in which the fibers 24, 26 and 28 are operatively connected to a plurality of infrared non-contact temperature sensors 21, 23 and 25 which are located external to the lance 12. The optical fibers 24, 26 and 28 are embedded in the outer surface of the lance 12 along the length of the lance 12 and are spaced at intervals of the lance 12 for taking a temperature reading at each location of the lance 12 when the lance 12 is extended near the tube bank 4. Although FIG. 4 only shows the use of three fibers and sensors, as many as thirty fibers and sensors may be utilized for taking a corresponding number of temperature readings.

Figure 4:
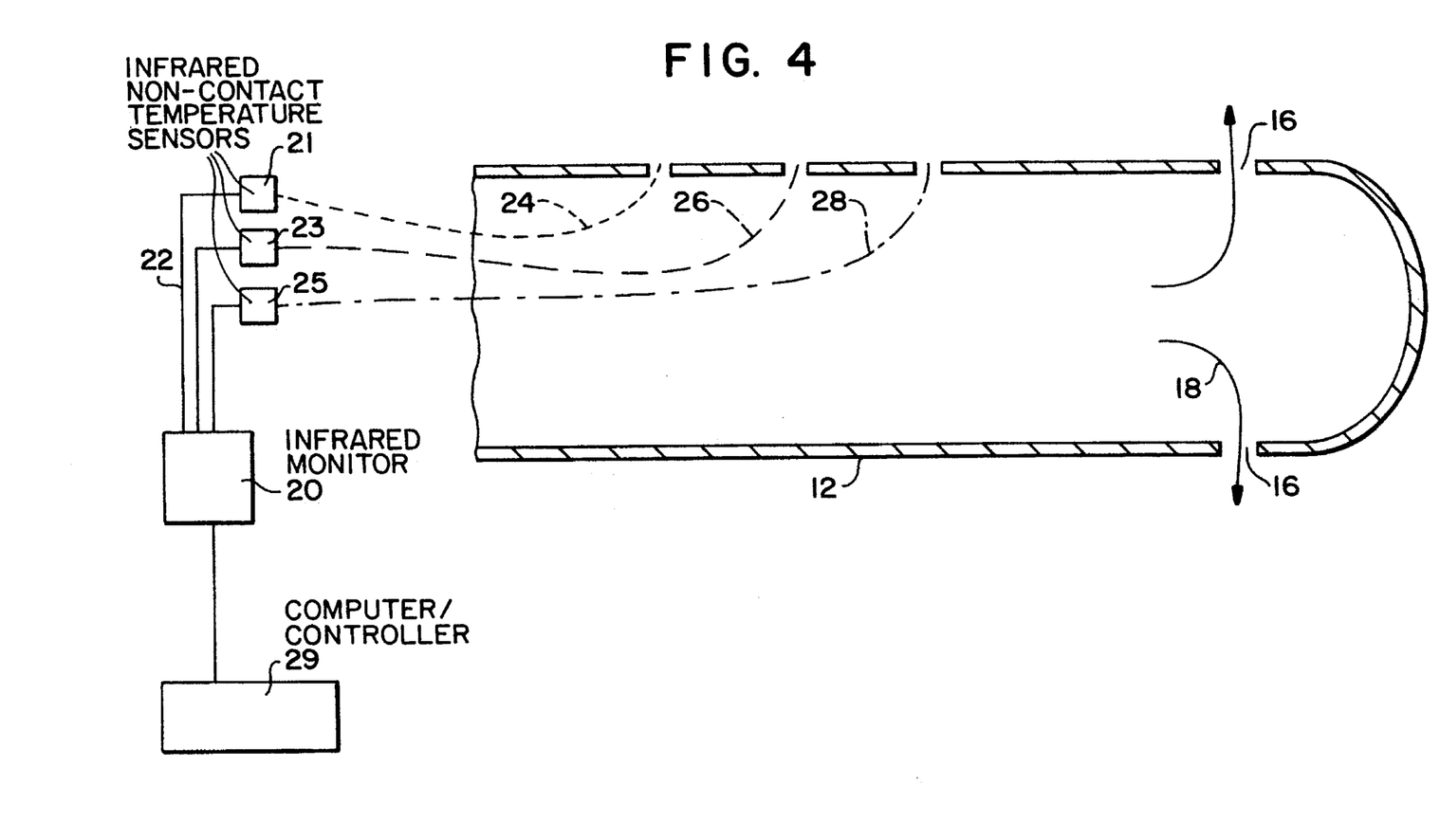
FIG. 4 is a schematic view illustrating a lance for the system of FIG. 3 utilizing a plurality of optical fibers for taking temperature readings.

Each infrared non-contact temperature sensor 21, 23 and 25 is operatively connected by connection line 22 to an infrared monitor 20 for sensing the infrared radiation signal transmitted from each infrared non-contact temperature sensor 21, 23 and 25. A computer 29 is operatively connected to the monitor 20 and determines a temperature reading at each location along the lance 12 based on the transmitted infrared radiation signal. In turn, the computer 29 calculates the temperature profile of the lance 12 based on the temperature readings at optical fiber locations 24, 26 and 28. Additionally, computer 29 determines the amount of build-up or deposits on the tube banks 4 (FIG. 1) by utilizing the internal temperature within the tube banks and the temperature profile measured near the exterior of the tube banks.

Deposits, build-up or soot are removed from the tubes 6 of the tube banks 4 (FIG. 2) through steam, water, cleaning liquid or air, schematically represented by reference numeral 18 which exits from the lance 12 at nozzle 16.

Figure 5:
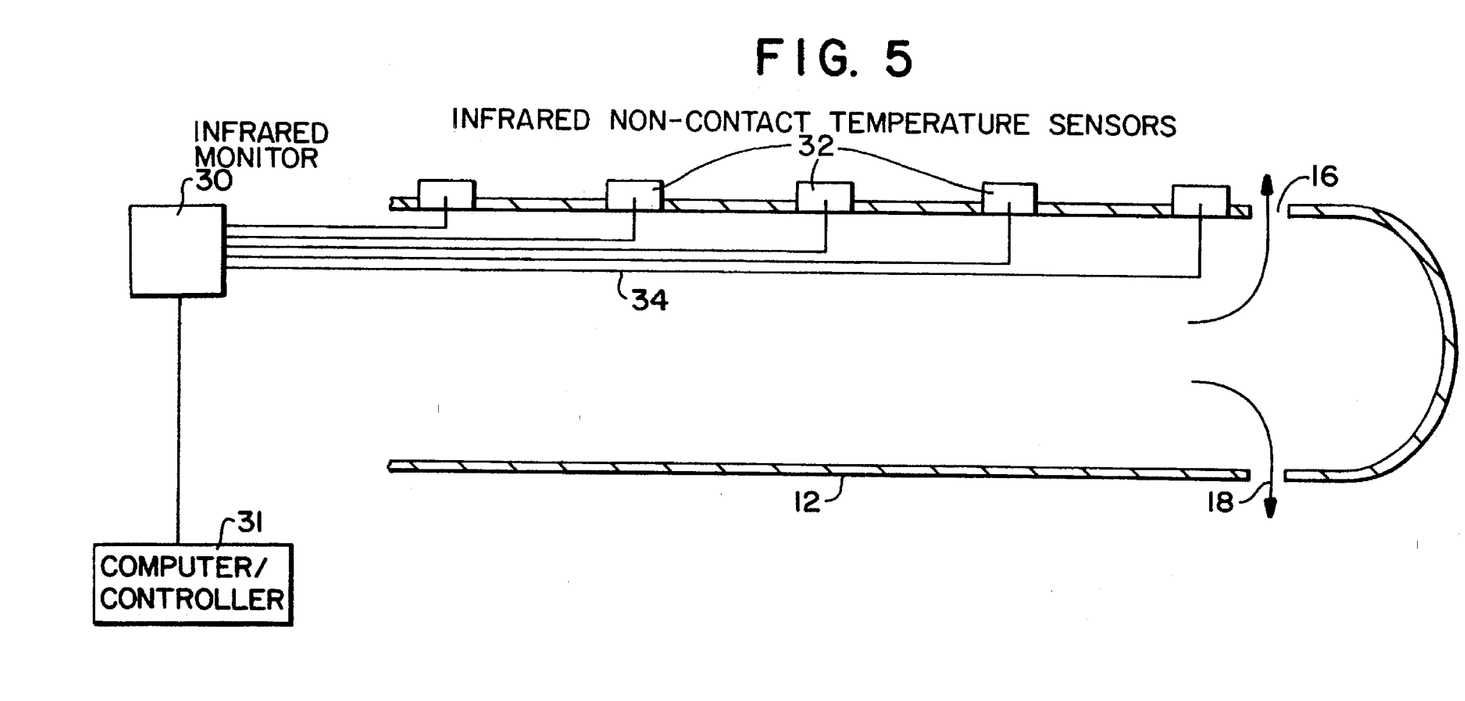
FIG. 5 is a schematic view of the lance of FIG. 3 utilizing a plurality of infrared non-contact temperature sensors for taking temperature readings.

A second embodiment (FIG. 5) for taking temperature readings includes a plurality of infrared non-contact temperature sensors 32 which are positioned upon the lance 12 at a distance of approximately 6 to 8 feet from the distal end of the lance 12. A monitor 30 is operatively connected with each infrared non-contact temperature sensor 32 by connection line 34. Accordingly, the monitor 30 receives the infrared transmission information provided by each infrared non-contact temperature sensor 32. A computer 31 is operatively connected to monitor 30 and determines the temperature reading at each location based on the infrared transmisivity. In turn, an overall temperature profile is calculated by the computer 31 based on the infrared transmissions from each infrared non-contact temperature sensor 32; and similar to the method described above, the computer 31 utilizes the temperature profile and input indicating internal temperature of the tubes in order to determine the amount of deposit or build-up on the tube banks 4.

Figures 7, 8:
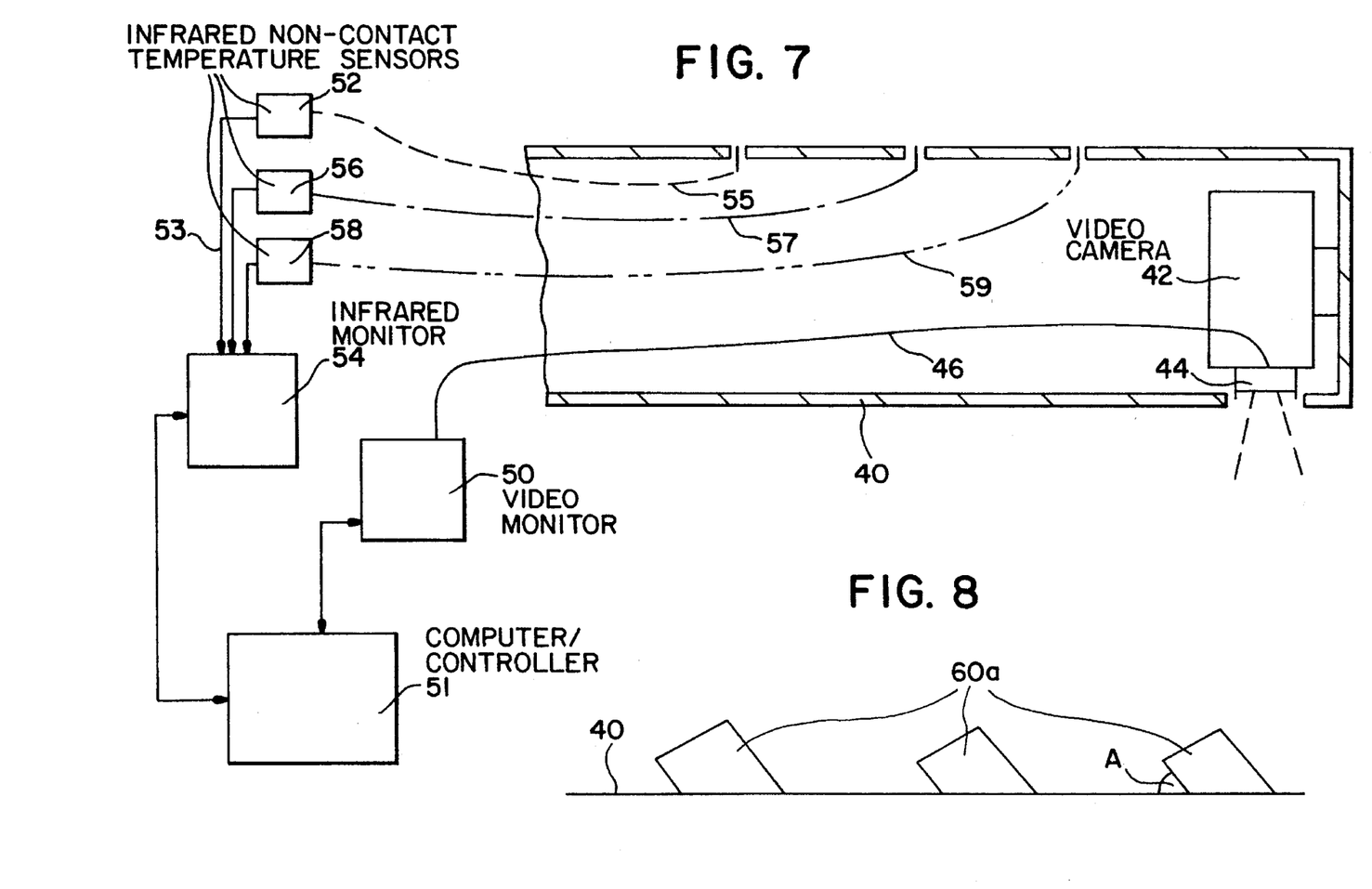
FIG. 7 is a schematic view illustrating an extension arm of a viewing camera having a plurality of optical fibers for taking temperature readings.
FIG. 8 is a schematic view illustrating a plurality of infrared thermocouple sensors in an angled configuration.

FIG. 7 illustrates another embodiment of the present invention in that an extension arm 40 for a video camera 42 is utilized for determining the temperature profile of the tube banks 4 (FIG. 1). A plurality of optical fibers 55, 57 and 59 are provided along the length of the extension arm 40 by exposing an end of the fibers 55, 57 and 59 at evenly spaced intervals along the length of the extension arm 40. The fibers 55, 57 and 59 are in turn operably connected to a plurality of infrared non-contact temperature sensors 52, 56 and 58. An infrared monitor 54 is operably connected by a connection line 53 to each infrared non-contact temperature sensor 52, 56 and 58 for sensing transmitted infrared radiation signals. A computer/controller 51 is operatively connected to monitor 54 for determining the temperature profile along the extension arm 40 and the amount of build-up on the tube banks 4 (FIG. 1) similar to the method described above. The optical fibers and sensors shown in FIG. 7 are not limited to the three fibers and sensors shown and as many as thirty fibers and sensors may be utilized.

Extension arm 40 includes the camera 42 rotatably mounted within and to the arm 40 by rotation mounting means 48 in order to enable the camera 42 to provide 360° viewing of the boiler 2 (FIG. 1). A video monitor 50 is utilized to view and record the view of the internals of the boiler 2 provided by lens 44 which is operatively connected to the monitor 50 by transmission line 46. Video monitor 50 is also operatively connected to computer 51 for control and information purposes.

Figure 6:
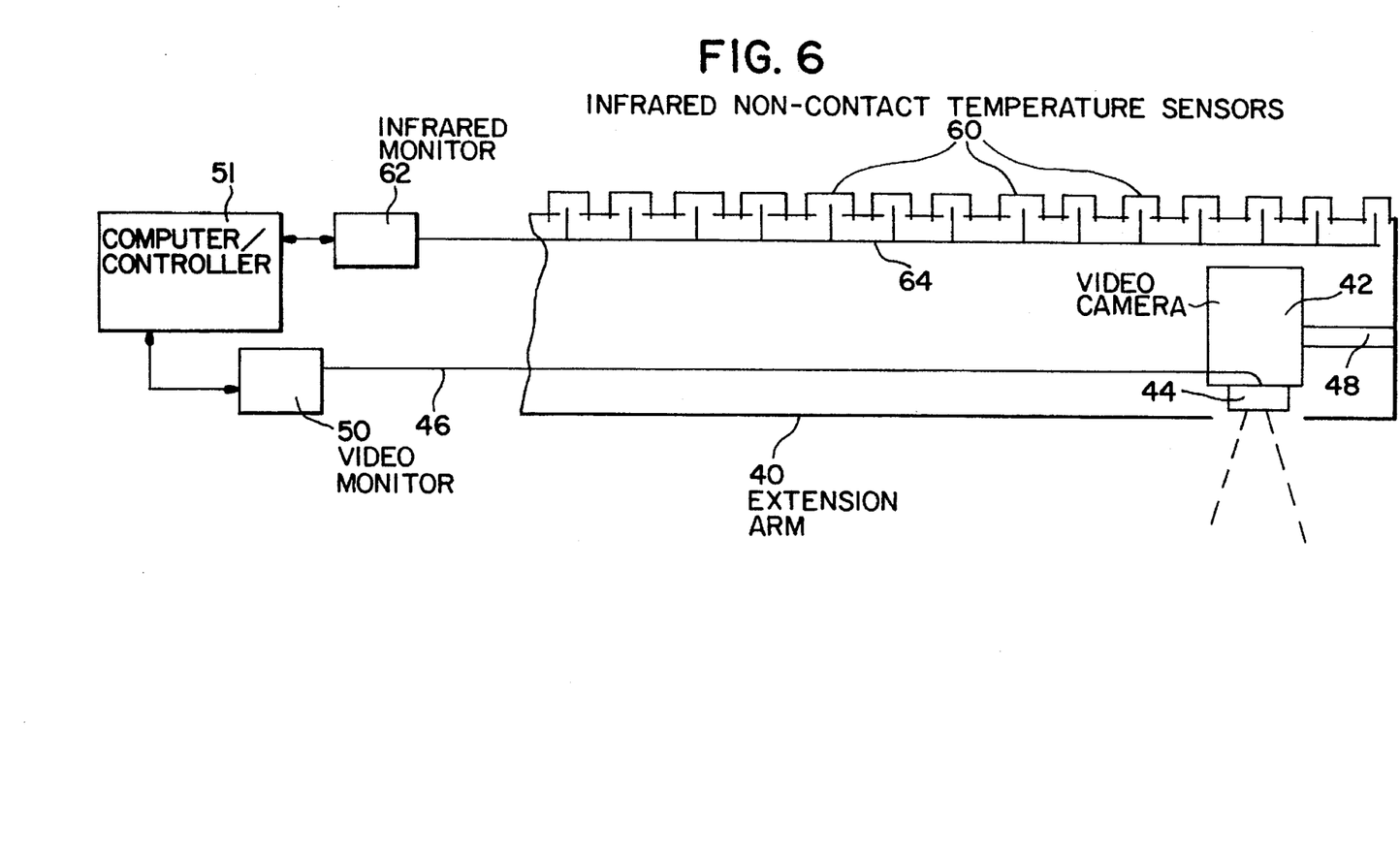
FIG. 6 is a schematic view illustrating an extension arm of a video camera having a plurality of infrared non-contact temperature sensors for taking temperature readings.

FIG. 6 illustrates a second embodiment for the video extension arm 40 in which a plurality of infrared non-contact temperature sensors 60 are spaced along the length of the extension arm 40 for providing infrared transmissions along transmission line 64 to infrared monitor 62. As many as thirty infrared non-contact temperature sensors may be used. The temperature profile and deposit build-up of the boiler bank tubes 6 are determined similar to the method described above used in conjunction with the lance embodiment through the use of computer 51 operatively connected to monitor 62.

FIG. 8 illustrates a plurality of infrared non-contact temperature sensors 60a located along the length of the extension arm 40 at an angle of inclination A in order to provide an angled temperature reading. The configuration illustrated in FIG. 8 can also be utilized for the lance embodiment of FIG. 5 and for the dedicated probe embodiment described hereinafter.

The infrared thermocouples 60 and 60a are aimed at the tube bank 4 (FIG. 1) and used to develop the temperature profile along the axis of the camera's extension tube 40. With a sufficient number of sensors 60, it is possible to distinguish a sensor 60 aligned directly focusing on the tube surfaces (and its deposits) from a sensor 60 aimed into the lanes between the tubes 6. Alternatively, the sensors 60 can be "back-raked" slightly (FIG. 8) so that the tube bank 4 is viewed at a slight angle A from the axis of the tube row. This arrangement yields an average temperature of the first several tubes in each row of the tube bank.

Figure 9:
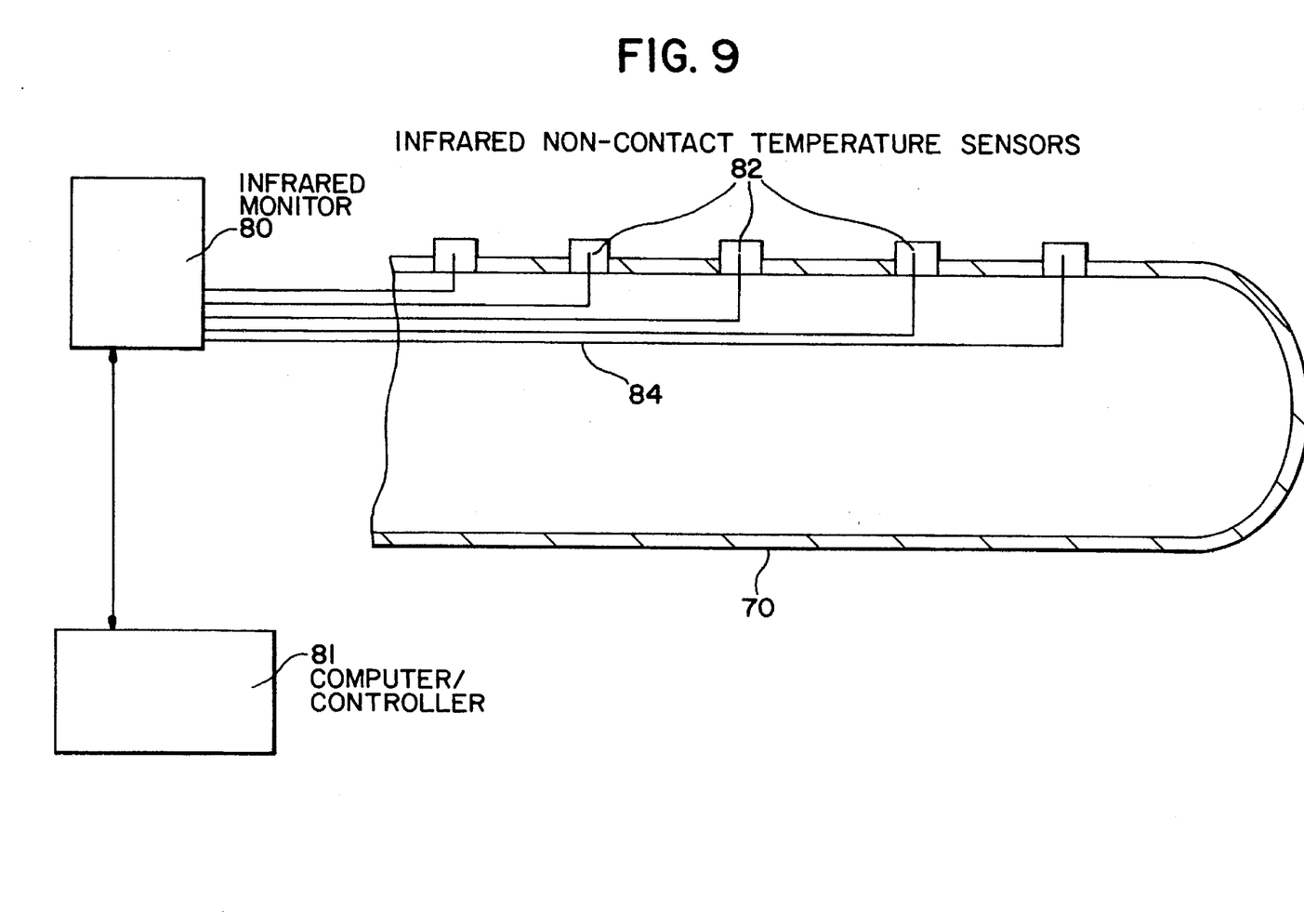
FIG. 9 is a schematic view illustrating a dedicated probe having a plurality of infrared non-contact temperature sensors for taking temperature readings.

Yet another embodiment of the present invention is illustrated in FIG. 9. A dedicated probe 70, which is similar in appearance and in method of insertion into the boiler 2 as lance 12, is employed for determining the temperature profile of the tube banks (FIG. 1). A plurality of infrared non-contact temperature sensors 82 are spaced along the length of the probe 70 for providing infrared transmission information along transmission lines 84 to infrared monitor 80. Like other embodiments described above, as many as thirty infrared non-contact temperature sensors 82 may be employed. A computer 81 is operably connected to the monitor 80, and the temperature profile and deposit build-up of the boiler bank tubes 6 are determined similar to the method described above in conjunction with the lance and the camera extension arm embodiments.

Figure 10:
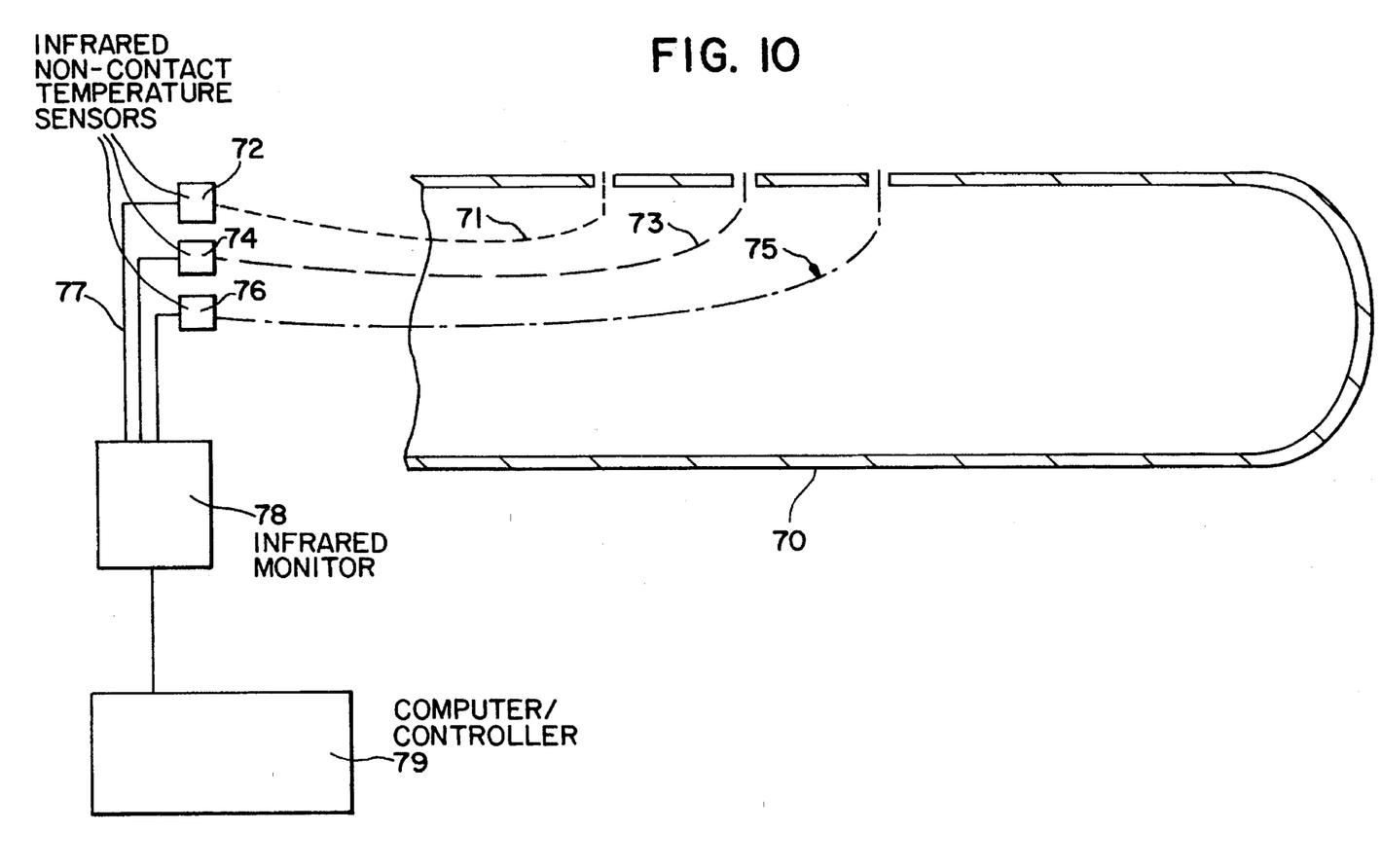
FIG. 10 is a schematic view illustrating a dedicated probe having a plurality of optical fibers for taking temperature readings.

FIG. 10 shows a second embodiment for the dedicated probe 70, which includes a plurality of optical fibers 71, 73 and 75 that are spaced along the length of the probe 70 with an end of each fiber exposed to the interior of the boiler 2. In a fashion similar to the lance and the camera extension arm embodiments described above, the optical fibers 71, 73 and 75 are operatively connected to a plurality of infrared non-contact temperature sensors 72, 74 and 76 which receive infrared radiation transmitted by the optical fibers. While only three optical fibers and three infrared sensors are shown in FIG. 10, as many as thirty fibers and thirty sensors may be employed. The plurality of infrared non-contact temperature sensors 72, 74 and 76 is operatively connected by connector lines 77 to an infrared monitor 78 which receives infrared transmission information. The monitor 78 is operatively connected to the computer 79 which determines the temperature profile and deposit build-up of the boiler bank tubes 6 by the method described above for the lance and the camera extension arm embodiments.

The surface temperature of the tubes 6 provides an immediate assessment of the surface fouling present. If the tubes are clean (bare tubes), the surface temperature will be close to the steam temperature inside the tubes which is readily estimated from known steam tables which are input into the computer 21, 31, 51, 79 and 81. If the tubes have accumulated thick deposits, the surface temperature will be close to the gas temperature at that point in the boiler 2 which can be measured utilizing known gas temperature devices. Most commonly, the measured temperature will be between these two extreme cases, and although the relationship is non-linear, the measurement will provide an estimate of the degree of deposit accumulation.

The use of the present invention provides before and after assessments of tube surface conditions when the various cleaning innovations are demonstrated in power and recovery boiler tube banks.

The present invention is distinguished over known temperature profile systems and methods by using an average deposit surface temperature, together with an estimate of the pipe wall temperature under the deposits and estimated thermal conductivity of the deposits to infer deposit thickness.

The portability of the present invention and immediate readout that is provided is most useful in avoiding biases associated with time-varying aspects of boiler operation that generally makes it difficult to obtain quantitative measurements of the effectiveness of boiler cleaning devices.

While specific embodiments of the invention have been shown and described in detail to illustrate the application of the principles of the invention, it will be understood that the invention may be embodied otherwise without departing from such principles.

What is claimed is:

1. A system for determining build-up on a plurality of tubes of a boiler, the system comprising:

extending means for being movably extendable into the boiler near the tubes and for removing build-up from the tubes;

optical fiber means for taking a separate temperature reading at a plurality of positions along a length of the extending means; and means for determining build-up on the tubes, based on the separate temperature readings taken from the length of the extending means.

2. The system according to claim 1, wherein the separate temperature means comprises a plurality of radiation sensor means for receiving radiation emitted by the tubes and build-up.

3. The system according to claim 2, wherein the radiation comprises infrared radiation.

4. The system according to claim 1, including a video means on the extension means for viewing the tubes.

5. A system for determining build-up on a plurality of tubes of a boiler, the system comprising:

extending means for being movably extendable into the boiler near the tubes and for removing build-up from the tubes;

a plurality of optical fibers for taking a separate temperature reading at a plurality of positions along a length of the extending means;

a plurality of infrared non-contact temperature sensors which are operably connected to the optical fibers; and means for determining build-up on the tubes, based on the separate temperature readings taken by the optical fibers, the build-up determining means including a computer and being operatively connected to the infrared non-contact temperature sensors.

6. A method for determining and removing build-up on a plurality of tubes of a boiler, the method comprising the steps of:

movably extending an arm having a length near the tubes of the boiler;

taking a separate temperature reading at a plurality of positions along the length of the arm by using a plurality of optical fibers which are operably connected to a plurality of infrared non-contact temperature sensors;

determining an amount of build-up on the tubes by operably connecting a computer to the infrared non-contact temperature sensors and by using the separate temperature readings taken from the arm; and removing build-up from the tubes, using the arm.

7. The method according to claim 6, including viewing the tubes by a video camera.

* * * * *